(12) United States Patent
Shoenfeld

(10) Patent No.: US 7,630,864 B2
(45) Date of Patent: Dec. 8, 2009

(54) TEMPERATURE AND HUMIDITY MONITORING FOR PHARMACY SHIPPING CRATE

(75) Inventor: Norman A. Shoenfeld, Livingston, NJ (US)

(73) Assignee: S&S X-Ray Products, Inc., Pen-Argyl, PA (US)

( * ) Notice: Subject to any disclaimer, the term of this patent is extended or adjusted under 35 U.S.C. 154(b) by 56 days.

(21) Appl. No.: 11/926,197

(22) Filed: Oct. 29, 2007

(65) Prior Publication Data
US 2008/0052044 A1 Feb. 28, 2008

Related U.S. Application Data

(63) Continuation-in-part of application No. 11/800,937, filed on May 8, 2007, which is a continuation-in-part of application No. 11/653,726, filed on Jan. 16, 2007, which is a continuation-in-part of application No. 11/391,386, filed on Mar. 29, 2006, now abandoned.

(51) Int. Cl.
*G06F 3/00* (2006.01)

(52) U.S. Cl. .................. 702/188; 702/177; 702/182; 702/187

(58) Field of Classification Search .................. 702/31, 702/41, 56, 119, 187, 188, 177, 182; 292/307 R; 340/572.4; 422/22; 701/32
See application file for complete search history.

(56) References Cited

U.S. PATENT DOCUMENTS

| | | | |
|---|---|---|---|
| 5,476,634 A * | 12/1995 | Bridges et al. | 422/22 |
| 7,089,099 B2 * | 8/2006 | Shostak et al. | 701/32 |
| 7,394,381 B2 * | 7/2008 | Hanson et al. | 340/572.4 |
| 2007/0120381 A1 * | 5/2007 | Ehrensvard et al. | 292/307 R |

* cited by examiner

*Primary Examiner*—Eliseo Ramos Feliciano
*Assistant Examiner*—Felix E Suarez
(74) *Attorney, Agent, or Firm*—Bernhard P. Molldrem, Jr.

(57) ABSTRACT

A monitor device is attached onto or inside a shipping crate for pharmaceutical shipments and monitors the temperature and/or humidity within the crate in transit to identify whether the contents are safe or compromised. A keyboard/display on the device provides an ID code that the recipient enters into a computer web page to communicate this ID code to the shipper or to a third-party agency. If the ID code represents a safe shipment, the shipper or third-party returns an acceptance message. If there has been a compromise, a different ID code is presented, and the web page instead returns a message to return the crate. A return envelope can be included for the recipient to return the monitor device to the shipper.

21 Claims, 1 Drawing Sheet

TEMPERATURE AND HUMIDITY MONITORING FOR PHARMACY SHIPPING CRATE

This is a continuation-in-part of my U.S. patent application Ser. No. 11/800,937, filed May 8, 2007, which is a continuation-in-part of my U.S. patent application Ser. No. 11/653,726, filed Jan. 16, 2007, which is a continuation-in-part of my U.S. patent application Ser. No. 11/391,386, filed Mar. 29, 2006 now abandoned. The same are incorporated herein by reference.

BACKGROUND OF THE INVENTION

This invention relates to containers used for shipping pharmaceuticals, especially those sensitive pharmaceuticals that can be compromised if temperature and/or humidity conditions are not properly observed during shipping. The invention is also concerned with a pharmacy shipping container that incorporates an electronic sensor that is attached onto a lid or cover of the crate, or is transported within the crate, and which can incorporate means for entering a receiving code or sequence, and transmitting a corresponding code or sequence electronically to a home station.

During transit, some pharmaceutical shipments need to be kept within a critical temperature range, and if so the crate or container needs to incorporate a system for monitoring the internal temperature. In addition to temperature monitoring, some pharmaceuticals need to be monitored for humidity, and some for both temperature and humidity. Some medicaments and medical products need to be at a temperature above ambient.

For transport of pharmaceuticals, or for use of pharmaceuticals in a mobile situation, there is a need for a sensing and monitoring device operates under battery power to provide a shipping chest or crate with a facility to monitor the quality of pharmaceuticals (e.g., temperature and/or humidity conditions) during transport. Then, if the temperature or humidity was outside the acceptable range during shipping, access can be monitored and controlled to the cabinet and to the possibly tainted medication, so that the quality of the sensitive contents can be assured.

Often it is desirable to track the temperature (and/or humidity) of the contents of the shipping chest or crate, and automatically to provide an alert warning if the temperature (or relative humidity) has been outside an acceptable range during transit. Other parameters can be tracked as well, e.g., carbon dioxide content, ammonia content, or other gas present on the inside of the container or crate.

A further need is for ensuring patient safety, i.e., to ensure any drugs that have not been kept at the proper storage conditions, e.g., having been outside of an acceptable temperature range, are not made available to patients until purity has been checked out by pharmacy staff.

The pharmaceutical industry has achieved a global reach and impact, with medicines and vaccines being shipped to all areas of the world. Many of these medicines and vaccines are temperature sensitive and have precise storage requirements. Unfortunately, during shipment the products can be subjected to extreme temperature and humidity changes, unforeseen delays during transit, especially international transit, and need for field delivery to remote points of use, several mode changes may occur. In addition, the pharmaceutical companies are subject to relentless cost pressures, so there is a need to make shipping and distribution as efficient as possible while ensuring that the products that are delivered are of consistent quality.

At the present time, most refrigerated medications are shipped in twelve-inch by twenty-four-inch insulated boxes, with ice. These can include a digital thermometer device that logs the temperature, but does not lock the box closed, and does not guarantee that any medication in the box that was subject to poor temperature control is isolated and not distributed to a patient. Some medications are shipped in a box or crate without ice, and are shipped in a refrigerated container. These boxes may have a special security tape that is intended to reveal tampering, but these are not locked containers, and there is no means included to prevent distribution of the medications if they had been subjected to adverse temperature (or humidity) conditions.

OBJECTS AND SUMMARY OF THE INVENTION

Accordingly, it is an object of the present invention to provide a shipping chest or crate with a facility to alert the recipient and also to alert the shipper or a third party oversight agency, if the temperature and/or humidity conditions have been outside a safe range or window. For purposes of the specification and claims, the term "shipping station" will be used to mean either the company or person who actually ships the crate and contents, as well as to mean a third-party agency that is tasked with oversight of the quality of the shipment.

It is another object to provide a shipping container or crate that automatically alerts the shipping agency, i.e., the shipper or third-party agency, if the pharmaceuticals are compromised at the time that the shipment is received.

A further object is to provide a shipping container or crate with a system providing a record of temperature conditions during shipment so as to help identify situations in the shipping process that may be causing adverse temperature conditions or other problems for the sensitive products being shipped.

Another object is to provide the electronic mechanism with or without a lock that can be used, e.g., for an authorized recipient to acknowledge receipt of the container or crate, and at the same time to relay to the shipping station or home station that the medications in the container or crate have been maintained within a safe range of temperature and/or humidity.

It is also an object to provide a means for providing security and ensuring safety of the contents of a shipment, by utilizing a website (hosted by the shipping station, e.g., the shipper or a third-party oversight agency), where codes provided on the monitor device are entered into a web screen, and the shipping station web page returns an appropriate message (i.e., good condition or possibly compromised condition), and which provides the shipping station with confirmation of the time and place of receipt of the shipment.

A more specific object is to provide a shipping crate or chest, of the type which is suitable for use in shipping of pharmaceuticals in a mobile refrigerated van or refrigerated shipping container, with temperature monitoring facilities to maintain a record of the temperature over time during transit.

In accordance with an aspect of the present invention, a monitor device is adapted to be attached or affixed onto a standard shipping crate adapted for mobile or portable use, i.e., for transporting or shipping pharmaceutical materials, with a cover or closure. The device is electronically controlled and is designed to work under battery power. The lock mechanism has metering and monitoring facilities, so that the storage conditions for the pharmaceuticals or other sensitive contents inside the shipping crate can be monitored during shipping. If the temperature and/or humidity is outside of the acceptable range during shipping, this will be automatically reported to the shipper when the recipient enters the code presented on the device. This feature alerts the shipper, and in some cases government authorities, of any compromised shipment, and may help prevent distribution of potentially contaminated or spoiled items. In an embodiment for this use, the crate or shipping container may be an insulated box containing ice or a box without ice intended to be transported in a refrigerated truck. The monitoring device on the crate (or inside it) can have a membrane switch, i.e., keypad/display, which provides an ID code that it displays as a sequence of numbers and/or letters. The recipient enters this sequence into the shipper's website or third-party agency's website to acknowledge receipt of the shipment. If the shipment has been maintained under acceptable humidity and temperature conditions, the code sequence that is to be relayed to the shipping station, i.e., the shipper or third-party agency, will indicate that the contents are in good condition. However, if the contents have been subjected to extreme temperatures or humidity changes, the device will provide a different ID code sequence that indicates that the materials may have been compromised. The entry of that ID code sequence into the shipper's web site will return instructions to return the box to the shipper. By accessing the monitoring device, e.g., with a USB cable, the shipper can obtain an audit trail of the time versus temperature and humidity conditions, and can identify the source of the problem. The software within the crate or container includes audit trail programming for recording time of shipping of the crate and of any accessing of the crate, and may also record the identity of each requesting person associated with handling of the crate. The software also keeps a time record of the temperature (and/or relative humidity) inside the unit When the software determines that the temperature in a given refrigerator has varied outside of the preset limits, the system will provide a coded sequence that corresponds to the temperature-compromised condition. This coded sequence is recognized by the shipper computer, and the latter automatically sends instructions to return the container and not to attempt opening it. The opening ID code changes with each shipment and may change at intervals, based on a security code or encryption system. The encryption software is present both in the shipping computer and in the control circuitry of the temperature/humidity monitor, as the codes generated are time sensitive. A key lock mechanism may be provided on the chest, but the device may also be used with non-locking crates.

The shipping container or crate may be constructed with insulation and a provision for holding ice, or alternatively it may simply enclose a standard refrigerated shipping container. The container or crate may also be designed for use within a refrigerated shipping container or vessel, and not need its own supply of ice or other chilling material.

The monitoring device may be constructed as a one-time-use item, and incorporated into or cemented to the lid of the shipping crate. Alternatively, the device may be attached over the box, e.g., with an incorporated shrink-wrap or strapping system. The use of shrink wrap for closing and sealing shipping containers is well known. In that case, the recipient may separate the monitoring device from the strapping or shrink wrap, and return the device to the shipper, using a return envelope that is included with the shipment inside the crate or container. The strapping system may be accomplished with strapping bands over the body and cover of the shipping container, and secured with mechanical sealing devices. There are temperature and humidity sensors disposed within the package, i.e., inside the shipping crate, so that the sensors will experience the same temperature and/or humidity conditions as the contents. These can be either disposable sensors or reusable sensors, returnable with the unit. For some applications, other qualities may be detected by the sensor, e.g., $CO_2$ content.

Software is provided for the shipper or third-party agency (i.e., the shipping station) and an interactive program is embedded into the monitor device. This allows the shipping station to provide, via Internet, a good-condition code sequence to the receiver when the shipment is received in good order. This arrangement can also identify a compromise situation, and then send a message not to attempt to open the crate but to return same to the shipper (or to another place, as instructed). This software may also provide for automated notification of regulatory authorities when a given shipment has been compromised, so that the product codes will be available, as well as suitable product alerts, in the event that the compromised pharmaceuticals are removed from the crate and distributed. Connection may be made using a USB or other cable, or with a wireless system, e.g., Bluetooth.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 1:
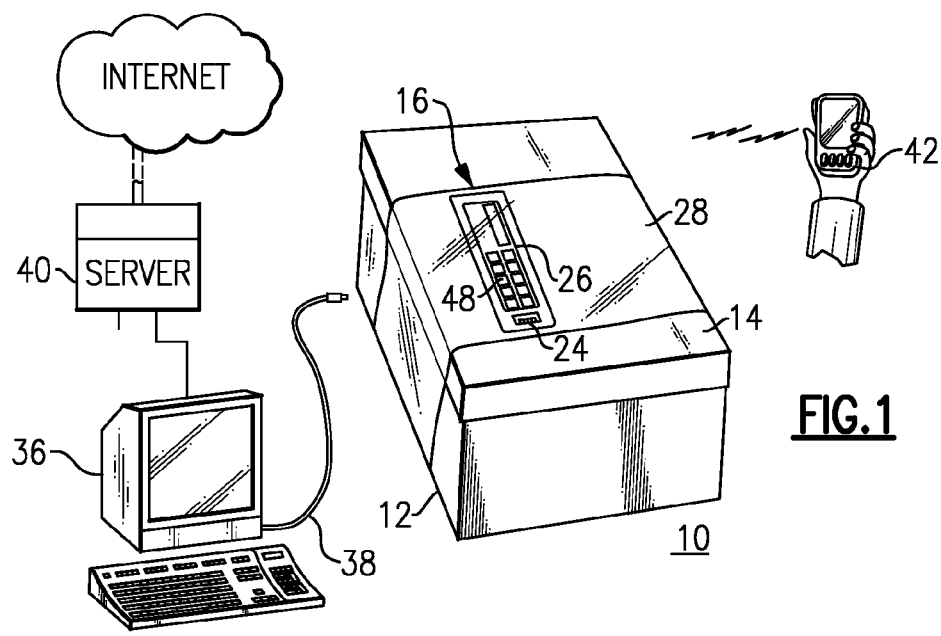
FIG. 1 is perspective view showing an embodiment of this monitor device of this invention here attached onto a pharmaceutical shipping crate or container.
Figure 2:
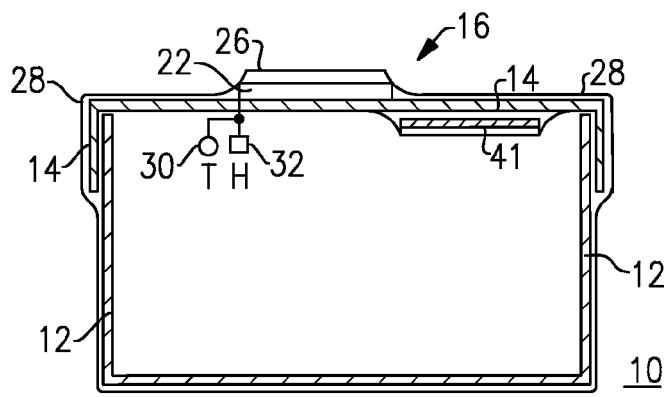
FIG. 2 is a sectional schematic view thereof.

With reference to the Drawing, and initially to FIGS. 1 and 2, a pharmaceutical shipping container or crate 10 is adapted for shipment of medications and pharmaceuticals that need to be kept refrigerated and/or need to be kept within a temperature range or humidity range. The crate 10 has an main enclosure or body 12 and a cover or lid 14. In the illustrated embodiment, the cover or lid 14 closes off the top of the crate, but it is also possible to have the crate openable at the front, where the cover may be hinged at the right to open from the left, or hinged at the left as a right-opening door. Mounted on the cover 14 is a temperature and humidity monitor device 16, including digital controller circuit 22, with a USB port 24 and a touch screen display and keypad mechanism 26. The a USB port 24 allows the controller circuit 22 to be connected electrically or electronically via a network, e.g., a LAN, that makes either a wired or wireless connection with a host computer server, to be discussed later.

In FIG. 2, the crate cover 14 and body 12 are shown schematically. In a practical embodiment, there can be compartments for ice or other cold source, as well as insulation in the walls of the crate.

The shipping agency is responsible for loading the crate and can seal the same for shipment using a sleeve of shrink wrap 28, which in this embodiment is incorporated with the monitor device 16. The digital controller circuit 22 includes built-in software that can maintain a log of the temperature and humidity inside the shipping crate during transit. Within the crate 10 or container are an internal temperature sensor probe 30 and a humidity sensor probe 32. In this embodiment, the controller circuit 22 is powered by an internal battery power. Power for operating the monitor device 16 and controller circuit 22 may also be provided via the USB port 24. In some embodiments, the monitor device 16 can simply be packed into the crate with the contents.

In a typical receiving environment, i.e., at a receiving warehouse or similar facility, a computer work station terminal 36 is present, which may be connected via a USB cable 38 to the USB port 24 on the device 16. The computer terminal 36 is also coupled, e.g., via a local server 40, to the Internet, where it can communicate with the shipping station's web site to confirm safe delivery of the crate. Alternatively, the receiver can communicate wirelessly with the crate electronics and the shipper using a hand held device 42. Otherwise, the numbers of the code on the monitor device may simply be read and keyed into the computer terminal 36.

FIG. 2 shows self-addressed return envelope 41, folded and retained in a pocket on the underside of the cover 14 within the shipping crate. When the shipment has been received and the recipient obtains a safe acceptance message, he or she can separate the monitor device 16 from the shipping crate and from the shrink wrap material, remove the envelope 41 from the interior of the crate, and then place the monitor device into the envelope, and return the same by mail or by courier to the shipper.

Figure 3:
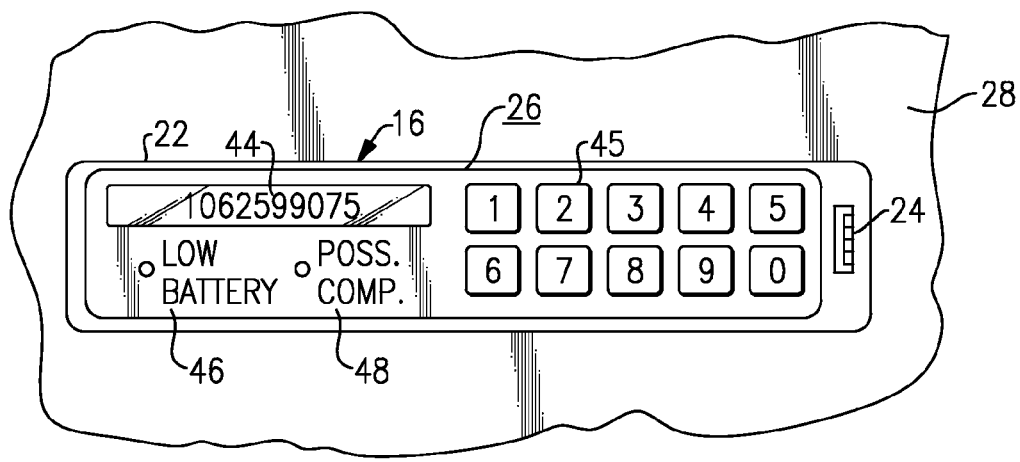
FIG. 3 is a plan view of monitor device, showing the touch-screen keypad thereof.

FIG. 3 shows one example of the touch-screen keypad device 26, here in the form of a membrane switch. A numeric display 44 at the upper left of the membrane switch shows a sequence of digits, here a ten-digit number, that is provided from the controller circuit 22. There are LED indicator lights 46 and 48, red and green, respectively, to indicate a low battery condition and/or safe or compromised (temperature and humidity) status of the crate. On the right is a pad 45 of ten touch-buttons or push-buttons, for the operator to enter a code sequence as directed by message received from the shipping location.

The temperature and humidity logs, stored in memory in the controller circuit 22, provide the ability to monitor pharmaceuticals when in transit, even when the unit is not connected to an external power supply. If the inside of the crate 10 was at all times during shipment within a prescribed temperature window (and, if appropriate, within a range of relative humidity), the stored program in the controller circuit 22 will output a coded signal to appear on the display 44 as a code sequence. However, if the temperature and/or humidity were outside of the acceptable range during shipping, the stored program in the controller circuit provides a different code sequence that is displayed on the display 44. The controller circuit 22 and the shipper's computer are both be programmed with encrypted software to generate and recognize code sequences that identify a safe arrival of the shipment or that identify a compromised or possibly compromised shipment. When the recipient turns on the touch screen, the displayed code sequence appears. Then the recipient enters this code sequence onto the shipping station's Internet web page that appears at the computer work station 36. If the code sequence represents a safe shipment, the shipping station's computer recognizes this and sends back an authorization to accept the shipment. The recipient then may open the cover 14 to access the pharmaceuticals inside. However, if the crate's code sequence represents a compromised shipment, i.e., when the temperature and/or humidity were outside of the safe window at some time during shipment, then when the code (shown on the display 44) is entered on the computer work station 36, the same will display a message that the crate may have been compromised and that the recipient is to send the crate back to the shipper immediately. In this way the system identifies any crate or container holding possibly compromised pharmaceuticals, to deter or block distribution of potentially tainted medication. As aforementioned, the crate 10 and its controller circuit can be connected by the USB cable 38 (or in some embodiments, wirelessly connected) with the computer work station 36 or with a local or wide area network, and the codes can be provided for identifying the quality of the shipment without needing to manually enter the displayed code sequence. The monitor screen of the computer work station 36, or hand-held device 42, will display safe arrival and success of the shipment, where the temperature and/or humidity have been maintained at safe levels. In the event that the number shown on the display 44 corresponds to a compromised shipment, the message to return the crate, unopened, back to the shipper, will appear on the screen of the work station 36 or hand-held device 42. At the same time, the fact of the compromised shipment, as well as the contents, i.e., lot number or other identifying information, is made known and can be transmitted automatically to authorities and pharmacies to prevent them from distributing compromised, and possibly unsafe, pharmaceuticals. Preferably, the shipping location will automatically generate alert messages, sent to the government authorities and to other users, identifying the crate contents with a product code, e.g., lot number and/or date codes, and a warning that such products are possibly tainted and should not be distributed or dispensed. Also, instead of the USB connection, it is possible to employ Bluetooth or another wireless system to interrogate the code when the crate arrives at the recipient location.

Similarly, it is possible to use RFID technology, with a programmable RFID code chip incorporated into the crate electronics. In the case of a normal or good shipment, the RFID chip would return one code, but if a shipment was out of temperature/humidity range, the chip would return a different coded signal to the scanner. This arrangement would require an RFID reader at the recipient site to obtain the coded information. A return of a "bad" code would then result in the shipper website responding with a "return crate to shipper" message. In this case, where the signal from the RFID chip (or the Bluetooth device) indicates a normal or safe shipment, the acceptance message can be sent wirelessly to the crate.

An optional feature is the use of a wireless temperature/humidity sensor. This would be placed within the insulated portion of the box, and would communicate wirelessly with the electronics within the box, but external to the insulation. This would eliminate any need to puncture or perforate the insulation to pass the wired sensor(s). Alternatively, other or additional sensors may be used, e.g., barometric pressure sensor and/or atmospheric gas composition sensor.

The controller circuit 22 may also be programmed to keep an audit history of all persons accessing the pharmaceutical crate, as well as times of access, in addition to keeping a history of the temperature and humidity conditions at all times during transit. The temperature and humidity charts may be displayed on the local computer monitor, for example. In some embodiments, these may be displayed on the touch-screen device 26.

The crates or containers of this invention may contain ice to maintain a cool internal temperature, or may be shipped within a refrigerated container or refrigerated chamber. In that case, different size boxes may be used for different size shipments. The acceptable temperature and humidity ranges or windows can be set electronically. The logs of temperature and humidity serve as a means of creating an audit history for the shipment. The monitor device may incorporate an alternative means of entering an access code.

The monitor device may also be employed without the temperature and humidity features for secure shipments of high interest items where authentication is needed upon receipt. When the shipment arrives at the destination, the recipient must first obtain a security-generated code, i.e., number, from the display 44 of the touch-screen device 26. This code number is then entered into the shipper website. If the generated code number appearing at display 44 indicates a shipment where the transport did not meet safety specifications, i.e., where there is evidence of unauthorized or forced opening, the website will notify the recipient (as well as the shipper) that the medicine is presumed compromised. The website also instructs the recipient as to the next step, i.e., to return the crate immediately to the pharmaceutical company. Then when the shipper receives the crate in the return shipment, the shipper will be able to inspect the contents.

This process as described above ensures that a secure transport chain is maintained, protecting the integrity of the medications at all times. If it turns out that the shipment without the proper receipt code is not returned, or is returned with indication of possible temperature or humidity compromise, and evidence of tampering or unauthorized opening, the pharmaceutical company and the governmental authorities would know that a batch of medication was tainted and was still distributed and used. The company can then send out warnings to users that certain date-coded and/or lot-coded medications may be tainted and are not to be used.

In addition, at time of shipment, the information on the packing list (i.e., contents, including lot numbers) preferably can also be entered into the aforementioned website. The website would then generate a shipping code for the container: this code would be different from the safe receipt code, but software in the container electronics would be able to use this to generate a unique time-sensitive safe receipt code which would be released from the website when the correct ID code is entered as input. This code can be entered into the container manually, or via a USB connection to an Internet-connected PC. If a faulty or incorrect ID code is entered (after some limited number of attempts) the crate will need to be returned to the sender. At the sender or shipper location, the USB connection can be employed for download of audit trail information, and can identify the time, location, and nature of the problem in transport.

The shipping crate can be or any standard design, either reusable or one-time-use, or may be fabricated of a durable plastic or metal (e.g., aluminum). The crate may contain insulation plus room for ice and the medications. Alternatively, the crate may have air holes for ventilation for use in a refrigerated truck. The crate may have an isolated ice or freezer pack compartment. The battery power may be from standard alkaline batteries, or from rechargeable cells, which may potentially be recharged via the USB connection.

This shipping crate monitor, i.e., the controller 22 thereof, achieves control over the transport chain, using Internet access. By mandating proper entry of a code to a secure website, the monitor device ensures reporting of improper transport and possibly tainted medications. The timing of the input also helps assure that the medication was received in timely fashion, and that there were no shipping delays in transit where the product was unrefrigerated.

Figure 4:
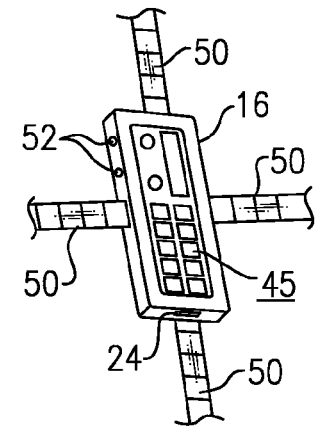
FIG. 4 shows another possible embodiment of the monitor device.

As shown in FIG. 4, the monitor device 16 can be provided with one or more sets of straps 50 for securing the device onto a crate or onto a package shipped within a crate. Here, sockets 52 are provided for plugging in detachable probes or sensors. The device can be provided without the straps or simply not using the straps, and packaging the monitor together with the shipment contents inside the crate.

In alternative embodiments of this invention, a locked shipping crate can be used in shipping of controlled materials, e.g., narcotics, where temperature and humidity do not need to be monitored, but where it important to ensure against tampering or unauthorized openings of the crate or container. In this case, the controller circuit incorporates suitable software with a provision for accepting an opening code from an authorized user so as to enable a lock mechanism to move and release a latch from engagement, so that the crate can be opened. Also, the monitor software would includes an audit trail provision for recording a history of the times and identities of person(s) opening the crate. The contents encoded within the controller circuit can be downloaded via the USB port 24, to identify whether there has been tampering or unauthorized opening. When the recipient returns the displayed code to the shipper (e.g., via Internet) the correct opening code for the lock is sent to the recipient only if there has been no tampering and no unauthorized openings. Then, the authorized recipient can open the cabinet. However, if the displayed code indicates that the tampering or unauthorized opening has occurred, the shipper will not provide the opening code, but instead will provide instructions to secure and/or return the crate. The shipper software can be programmed to automatically inform the appropriate government authorities of a possibly compromise of the controlled substance.

In many cases, a lock would not be used but the crate would be secured shut during shipment, e.g., sealed with the shrink wrap sleeve 28, or equivalently with a band or strap with a mechanical seal. This would provide a tamper-evident closure. The monitoring and notification features would be retained, for example in the transport of "biologicals"—transplant organs. In such case, the receiving surgeon should be able to confirm the status of shipment conditions, but the recipient is not prevented from using the transplant organ if the surgeon determines, upon inspection and in consideration of the caution about possible shipment delays and temperature or pressure deviations, that the organ is nonetheless acceptable.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

I claim:

1. A monitoring device adapted to be affixed onto or placed within a shipping crate for transport from a shipping station to a recipient at a recipient location, and holding as contents thereof sensitive materials; the monitoring device identifying for the recipient and the shipping station, upon delivery, whether said contents have been subjected to compromising conditions during transit of the crate, with said shipping crate having a body in which said sensitive materials are to be stored and shipped and a cover for closing off the body of the shipping crate; the monitoring device comprising:

means securing the monitoring device onto or within the shipping crate;

sensor means disposed inside the shipping crate for sensing one or more conditions of the contents of said shipping crate during transit;

control circuit means coupled to said sensor means and having embedded software therein to maintain a log of said one or more conditions during transit, said control circuit means being adapted to generate a safe-shipment coded sequence representing a safe condition for said contents and to generate a different compromised-shipment coded sequence representing a compromised conditions of said contents, each said coded sequence being based on sensor-provided information concerning the contents of said shipping crate during transit;

means for presenting one or the other of said coded sequences, wherein the control circuit means presents one or the other of said safe-shipment coded sequence and said compromised shipment coded sequence; and means for transmitting the safe-shipment or compromised-shipment coded sequence as presented by said control circuit to said shipping station.

2. The monitoring device according to claim 1, wherein said sensor means includes a temperature monitor having a probe sensing temperature inside said shipping crate during transit; and said control circuit means being connected to said probe and being operative to maintain the log of temperature within said crate during transit, and providing said coded sequence based on the log of temperature received from said temperature monitor.

3. The monitoring device according to claim 1, wherein said sensor means includes a humidity monitor having a probe sensing a humidity level inside said shipping crate, the monitor being coupled with said control circuit means for communicating said humidity level thereto, the control circuit means being operative to maintain the log of humidity level within said crate during transit, and providing said coded sequence based on the log of humidity level.

4. The monitoring device according to claim 1, said embedded software within said control circuit means further including software which includes audit trail means for recording readings of said one or more conditions and times of reading of said one or more conditions during transit.

5. The monitoring device according to claim 1, wherein said means for presenting includes display means on a visible portion of said monitoring device for displaying the one or other of said coded sequences as a sequence of digits.

6. The monitoring device crate according to claim 1, wherein said control circuit means includes audit trail software for recording a time history of temperature of the inside of said shipping crate during transit.

7. The monitoring device crate according to claim 1, wherein said control circuit means includes audit trail software for recording a time history of humidity inside said shipping crate during transit.

8. The monitoring device according to claim 1, wherein said means for presenting one or the other of said coded sequences includes a USB interface on said monitoring device.

9. The monitoring device according to claim 1, wherein said means to permit the recipient to enter a predetermined recipient code sequence comprises a control and display interface device which includes keypad buttons thereon for entering said recipient code sequence, and a display area showing at least said coded sequences.

10. The monitoring device crate according to claim 1, comprising a closure device formed of a closure material incorporated therein and sealing the cover and body of the shipping crate during transit.

11. The monitoring device according to claim 10, wherein said closure device includes a sleeve of shrink-wrap material.

12. The monitoring device according to claim 10, wherein said closure device includes strapping bands and a mechanical seal therefor.

13. The monitoring device according to claim 1, further comprising a return envelope contained within the body of said shipping crate for returning the monitoring device to the shipping location after receipt of the shipping crate.

14. A method of ensuring safe transport of a quantity of a sensitive material in a shipping crate from a shipping station to a recipient at a receiving location, in which the shipping crate includes:

a body in which sensitive materials are to be stored and shipped, and a cover which closes on said body;

with the method employing a monitor device, with one or more sensors situated within said shipping crate for detecting at least one environmental parameter of the interior of the shipping crate during transit; the monitor device including control circuit means disposed on an exterior of said shipping crate, communicating with said one or more sensors, and including means suitably programmed with embedded software to maintain a log of said one or more parameters during transit, and means for presenting a coded sequence generated by said embedded software, wherein the control circuit means generates a safe-shipment coded sequence when the log of said environmental parameters during transit represents a safe condition for said contents and a different compromised-shipment coded sequence when the log of said environmental parameters during transit represents a compromised conditions of said contents during transit; and means for electronically transmitting the one or the other of said safe-shipment and compromised-shipment coded sequences from the receiving location to said shipping station;

the method comprising:

(1) sending the crate from said shipping location to said receiving location;

(2) at said receiving location, obtaining from said monitoring device said coded sequence and transmitting said coded sequence presented on said monitoring device to said shipping station;

(3) where said coded sequence represents a safe condition of the contents of said crate, said shipping location transmitting to said receiving location a safe acceptance message; but (4) where said coded sequence represents a compromised condition of the contents of the shipping crate, said shipping station transmitting to said receiving location a message indicating possible compromise of said opening code and instructions for safe disposition of said shipping crate and the contents thereof.

15. The method of claim 14, further comprising providing at said receiving location, from said suitably programmed circuit means, an audit trail history of the conditions of said crate logged in the monitoring device during transit.

16. The method of claim 15, wherein said audit trail history includes a time record of temperature within said shipping crate logged in the monitoring device during transit.

17. The method of claim 15, wherein said audit trail history includes a time record of humidity within said shipping crate logged in the monitoring device during transit.

18. The method of claim 14, wherein a computer processor at said shipping location and the suitably programmed circuit means of said monitoring device each include encryption software for automatically changing over time said safe-shipment coded sequence representing safe conditions during transit.

19. The method of claim 14, further comprising, in the case in which the coded sequence represents a compromised condition, said shipping location automatically generating alert messages, identifying the contents of said crate by product code, alerting other customers that such contents are possibly compromised and are not to be used.

20. A method of safe shipment of a sensitive item in a shipping crate from a shipping station to a receiving location, in which the shipping crate includes:

> a body in which sensitive materials are to be stored and shipped and a cover which closes on said body;
> 
> closure means on said shipping crate for securing the cover closed on the body;
> 
> a monitor device held in place on or disposed within said shipping crate, including suitably programmed circuit means containing embedded software to generate a safe-shipment coded sequence to be transmitted to said shipping station and representing a safe condition for said contents and generating a different compromised-shipment coded sequence to be transmitted to said shipping station and representing a compromised conditions of said contents based on conditions of said shipping crate during transit;
> 
> the method comprising:
> 
> > sending the crate, secured with said closure means, from said shipping location to said receiving location;
> > 
> > at said receiving location,
> > 
> > > obtaining from said crate said one of said safe-shipment coded sequence and compromised-shipment coded sequence and transmitting same to said shipping station;
> > 
> > where said coded sequence is said compromised-shipment coded sequence and represents a compromised condition of the contents of the shipping crate, said shipping station transmitting to said receiving location a message providing a possible compromise message to the recipient; but
> > 
> > where said coded sequence is said safe-shipment coded sequence and represents a safe condition of the contents, said shipping station transmitting to said receiving location a safe acceptance message.

21. The method according to claim 20, further comprising removing said monitor device from said shipping crate, removing a return envelope from within the shipping container, placing the monitor device in an return envelope, and returning the monitor device in said shipping envelope to said shipping station.

* * * * *